United States Patent
Schmid et al.

(10) Patent No.: US 7,298,013 B2
(45) Date of Patent: Nov. 20, 2007

(54) COMPOUND USED TO FORM A SELF-ASSEMBLED MONOLAYER, LAYER STRUCTURE, SEMICONDUCTOR COMPONENT HAVING A LAYER STRUCTURE, AND METHOD FOR PRODUCING A LAYER STRUCTURE

(75) Inventors: Guenter Schmid, Hemhofen (DE); Marcus Halik, Erlangen (DE); Hagen Klauk, Stuttgart (DE); Ute Zschieschang, Stuttgart (DE); Franz Effenberger, Stuttgart (DE); Markus Schutz, Stuttgart (DE); Steffen Maisch, Gerlingen (DE); Steffen Seifritz, Gladbeck (DE); Frank Buckel, Krefeld (DE)

(73) Assignee: Infineon Technologies AG, Munich (DE)

( * ) Notice: Subject to any disclaimer, the term of this patent is extended or adjusted under 35 U.S.C. 154(b) by 142 days.

(21) Appl. No.: 11/313,250

(22) Filed: Dec. 20, 2005

(65) Prior Publication Data

US 2006/0175603 A1  Aug. 10, 2006

Related U.S. Application Data

(63) Continuation of application No. PCT/DE2004/001318, filed on Jun. 18, 2004.

(30) Foreign Application Priority Data

Jun. 20, 2003 (DE) ............... 103 28 811

(51) Int. Cl.
*H01L 29/76* (2006.01)
(52) U.S. Cl. ............... 257/410; 257/40; 257/E51.007; 257/E29.291; 257/E29.294; 257/E21.299; 257/E21.44; 438/99; 438/158; 977/936

(58) Field of Classification Search ............ 257/410, 257/40, E51.007, 29.291, 29.294, 21.299, 257/21.414; 438/158, 99; 977/936
See application file for complete search history.

(56) References Cited

U.S. PATENT DOCUMENTS 4,539,061 A  9/1985  Sagiv (Continued)

FOREIGN PATENT DOCUMENTS

DE  198 15 220 A1  9/1999

(Continued)

OTHER PUBLICATIONS

Tillman, N., et al., "Incorporation of Phenoxy Groups in Self-Assembled Monolayers of Trichlorosilane Derivatives: Effects on Film Thickness, Wettability, and Molecular Orientation," J. Am. Chem. Soc., vol. 110, No. 18, 1988, pp. 6136-6144. (XP-002299960).

(Continued)

*Primary Examiner*—George R. Fourson
*Assistant Examiner*—Julio J. Maldonado
(74) *Attorney, Agent, or Firm*—Slater & Matsil, L.L.P.

(57) ABSTRACT

Embodiments of the invention provide a semiconductor component and a method of manufacture thereof. A semiconductor component comprises: a gate electrode layer adjacent a substrate, and a gate dielectric layer adjacent the gate electrode layer. The gate dielectric layer comprises a monolayer of at least one compound, wherein the compound has an aromatic or a condensed aromatic molecular group. The molecular group is capable of π-π interactions, which stabilize the monolayer. In an embodiment, the semiconductor component is an organic field effect transistor (OFET). In an embodiment of the invention, a method includes forming the monolayer using a liquid phase immersion process.

20 Claims, 11 Drawing Sheets

U.S. PATENT DOCUMENTS

| | | | |
|---|---|---|---|
| 5,686,549 | A | 11/1997 | Grainger et al. |
| 5,728,431 | A | 3/1998 | Bergbreiter et al. |
| 5,783,648 | A | 7/1998 | Bergbreiter et al. |
| 6,433,359 | B1 * | 8/2002 | Kelley et al. ............ 257/40 |
| 2001/0055768 | A1 | 12/2001 | Nakamura et al. |
| 2002/0057398 | A1 | 5/2002 | Ogawa |
| 2002/0167003 | A1 | 11/2002 | Campbell et al. |
| 2003/0157798 | A1 | 8/2003 | Gabric et al. |
| 2003/0175551 | A1 | 9/2003 | Smith et al. |
| 2004/0241590 | A1 | 12/2004 | Park et al. |

FOREIGN PATENT DOCUMENTS

| | | |
|---|---|---|
| DE | 697 08 331 T2 | 7/2002 |
| DE | 102 07 130 A1 | 9/2003 |
| EP | 0 978 499 B1 | 11/2001 |
| EP | 1 179 863 A2 | 2/2002 |
| JP | 2003-092411 A | 3/2003 |
| WO | WO 02/086979 A1 | 10/2002 |
| WO | WO 03/023517 A1 | 3/2003 |
| WO | WO 03/077327 A1 | 9/2003 |

OTHER PUBLICATIONS

Tillman, N., et al., "A Novel Self-Assembled Monolayer Film Containing a Sulfone-Substituted Aromatic Group," Langmuir, vol. 6, No. 9, 1990, pp. 1512-1518. (XP-002300327).

Collet, J., et al., "Nano-field effect transistor with an organic self-assembled monolayer as gate insulator," Applied Physics Letters, vol. 73, No. 18, Nov. 2, 1998, pp. 2681-2683.

Lackowski, W.M., et al., "Micron-Scale Patterning of Hyperbranched Polymer Films by Micro-Contact Printing," J. Am. Chem. Soc., vol. 121, No. 6, 1999, pp. 1419-1420 (published on the web Feb. 2, 1999).

Ghosh, P., et al., "Covalent Grafting of a Patterned, Hyperbranched Polymer onto a Plastic Substrate Using Microcontact Printing," J. Am. Chem. Soc., vol. 121, No. 36, 1999, pp. 8395-8396. (published on the web Aug. 31, 1999).

Collet, J., et al., "High anisotropic conductivity in organic insulator/semiconductor monolayer heterostructure," Applied Physics Letters, vol. 76, No. 10, Mar. 6, 2000, pp. 1339-1341.

Collet, J., et al., "Low-voltage, 30 nm channel length, organic transistors with a self-assembled monolayer as gate insulating films," Applied Physics Letters, vol. 76, No. 14, Apr. 3, 2000, pp. 1941-1943.

Gershevitz, O., et al., "Molecular Monolayer-Mediated Control over Semiconductor Surfaces: Evidence for Molecular Depolarization of Silane Monolayers on $Si/SiO_x$," J. Am. Chem. Soc., vol. 125, No. 16, 2003, pp. 4730-4731. (published on the web Apr. 1, 2003) (XP-002299959).

Turgeman, R., et al., "Oriented Growth of ZnO Crystals on Self-Assembled Monolayers of Functionalized Alkyl Silanes," Crystal Growth & Design, vol. 4, No. 1, 2004, pp. 169-175. (published on the web Sep. 26, 2003) (XP-002299963).

Gershewitz, O., et al., "Effect of Molecule-Molecule Interaction on the Electronic Properties of Molecularly Modified $Si/SiO_x$ Surfaces," J. Phys. Chem. B, vol. 108, No. 2, 2004, pp. 664-672. (published on the web Dec. 13, 2003) (XP-002299962).

* cited by examiner

FIG 12

| Substrate | Gate | SAM | Active layer | Contact | Carrier mobility | Threshold voltage | Subthreshold voltage | $I_D$ on/off | $I_D/I_G$ | $J_G$ ($V_{GS} = -1V$) |
|---|---|---|---|---|---|---|---|---|---|---|
| UZ-31 | Si | PhO | Pentacene | top | 0.9 cm$^2$/V-s | -0.6 V | 135 mV/dec | 10$^4$ | 2.8 | 7x10$^{-5}$ A/cm$^2$ |
| UZ-33 | Si | PhO | Pentacene | bottom | 0.2 cm$^2$/V-s | -0.1 V | 240 mV/dec | 10$^3$ | 10$^2$ | |
| UZ-35 | Si | OTS | Dec-6T-Dec | top | 0.04 cm$^2$/V-s | 0 V | 200 mV/dec | 10$^3$ | 10$^2$ | 2x10$^{-7}$ A/cm$^2$ |
| UZ-36 | Si | OTS | Pentacene | top | no FE | | | | | 5x10$^{-3}$ A/cm$^2$ |
| UZ-37 | Si | | Dec-6T-Dec | top | no FE | | | | | 2x10$^{-3}$ A/cm$^2$ |
| UZ-43 | Al | OTS | Dec-6T-Dec | top | 0.03 cm$^2$/V-s | -0.9 V | 360 mV/dec | 10$^3$ | 5.3 | 2x10$^{-8}$ A/cm$^2$ |
| MH-357 | Si | PhO | Pentacene | top | 1 cm$^2$/V-s | -1.3 V | 100 mV/dec | 10$^5$ | 10$^4$ | 2x10$^{-9}$ A/cm$^2$ |
| MH-362 | Si | PhO | Pentacene | bottom | 0.05 cm$^2$/V-s | -0.7 V | 140 mV/dec | 10$^4$ | 10$^3$ | 3x10$^{-8}$ A/cm$^2$ |

US 7,298,013 B2

COMPOUND USED TO FORM A SELF-ASSEMBLED MONOLAYER, LAYER STRUCTURE, SEMICONDUCTOR COMPONENT HAVING A LAYER STRUCTURE, AND METHOD FOR PRODUCING A LAYER STRUCTURE

This application is a continuation of co-pending International Application No. PCT/DE2004/001318 filed Jun. 18, 2004, which designated the United States and was not published in English, and which is based on German Application No. 103 28 811.2 filed Jun. 20, 2003, both of which applications are incorporated herein by reference.

TECHNICAL FIELD

The invention relates to semiconductor manufacturing and more particularly to organic field effect transistors (OFET) and semiconductor components having organic compounds, organic monolayers, and organic layer structures.

BACKGROUND

Field effect transistors based on organic semiconductors (OFET) are of interest for a large number of electronic applications. In particular, low manufacturing costs, flexible or unbreakable substrates or the production of transistors and integrated circuits over large active areas are possible therewith. For example, organic field effect transistors are suitable as pixel control elements in active matrix screens or for the production of extremely economical integrated circuits, as used, for example, for the active marking and identification of products and goods.

Since complex circuits can be built up using organic field effect transistors, there are numerous potential applications. Thus, for example, the introduction of RF-ID (RF-ID: radio frequency identification) systems based on this technology is considered a potential replacement for the bar code, which is susceptible to faults and can be used only in direct optical contact with the scanner. Passive RF-ID systems obtain their energy from the incident alternating field. The possible distance between reader and transponder depends on the radiant power and the energy requirement of the transponder. Silicon-based transponders therefore operate at supply voltages of about 3 V. Products which contain a silicon-based chip are too expensive for many applications. For example, a silicon-based identification tag is not suitable for the marking of foods (price, expiry date, etc.).

Organic field effect transistors usually consist of at least four different layers applied one on top of the other: a gate electrode, a dielectric, a source-drain contact layer and an organic semiconductor. The sequence of the layers may vary. To ensure the functionality, the individual layers must be structured, which is relatively complicated.

Polymers or organic semiconductors offer the potential of being able to use cheap printing techniques for their structuring and application. The gate potential for controlling the organic field effect transistors can be chosen to be all the lower but thinner in the form in which the gate dielectric (i.e. a dielectric layer) can be produced.

In polymer electronics, the thickness of the gate dielectric is generally optimized so that the solution of a polymer is spun out or printed on increasingly thinly (top-down). However, this procedure encounters its limits when it is intended to achieve layer thicknesses of less than 50 nm.

It is known that layers for organic field effect transistors can be built up by means of self-assembled layers comprising molecular monolayers (SEM: self-assembled monolayers).

In the articles by J. Collet, D. Vuillaume; "Nano-field effect transistor with an organic self-assembled monolayer as gate insulator", Applied Physics Letters 73 (1998) 2681; J. Collet, S. Lenfant, D. Vuillaume, O. Bouloussa, F. Rondelez, J. M. Gay, K. Kham, C. Chevrot; "High anisotropic conductivity in organic insulator/semiconductor monolayer heterostructure", Applied Physic Letters 76 (2000) 1339, and J. Collet, O. Tharaud, A. Chapoton, D. Vuillaume; "Low-voltage, 30 nm channel length, organic transistors with a self-assembled monolayer as gate insulating films", Applied Physics Letters 76 (2000) 1941, which describes such layers.

These layers are also discussed in the articles by Pradyt Ghosh, Richard M. Crooks; "Covalent Grafting of a Patterned", Hyperbranched Polymer onto Plastic Substrate Using Microcontact Printing", J. Am. Chem. Soc. 121 (1999) 8395-8306, and William M. Lackowski, Pradyut Ghosh, Richard M. Crooks; "Micron-Scale Patterning of Hyperbranched Polymer Films by Micro-Contact Printing;", J. Am. Chem. Soc. 121 (1999) 1419-1420 and Jacob Sagiv; "Process for the production of built-up films by the stepwise adsorption of individual monolayers", and U.S. Pat. No. 4,539,061 (1985).

The articles by Collet et al. describe materials that make it possible to use transistors having SAM layers. Vinyl-terminated silanes have anchor groups on hydroxyl-containing substrate surfaces to form an SAM. This is subsequently chemically aftertreated in order to bind further molecules chemically to the SAM (cf. article by Sagiv et al.), or surfaces which permit further processing are produced (cf. article by Collet, Tharaud et al.).

It is disadvantageous that these layers do not form a dense dielectric layer without aftertreatment. The chemical aftertreatments used converts only 70 to 90% of the terminal groups in a reaction time of 48 to 120 hours. This chemical aftertreatment takes too long for the production of large quantities.

In principle, it is also possible to bind polymers via a plurality of coordination sites to a surface (Self-Assembled Polymers). This is disclosed in U.S. Pat. No. 5,728,431, U.S. Pat. No. 5,783,648 (1998) and U.S. Pat. No. 5,686,549.

SUMMARY OF THE INVENTION

It is the object of the present invention to provide means and methods for the efficient production of a semiconductor component, in particular of an organic field effect transistor.

An embodiment of the invention provides a compound used to form a self-assembled monolayer, preferably particular a monolayer for a semiconductor component. The compound preferably comprises a molecular group capable of a π-π interaction with other compounds of the same type and/or compounds of another type for stabilizing the monolayer. The π-π interaction permits the mutual bonding of the individual molecules in the monolayer with one another.

Preferably, the molecular group capable of a π-π interaction has an aromatic or a condensed aromatic having up to five ring systems, in particular a naphthalene, anthracene, naphtacene, pentacene, biphenyl, terphenyl, quaterphenyl and/or quinquephenyl. In other embodiments, the molecular group capable of a π-π interaction has at least one of the following groups:

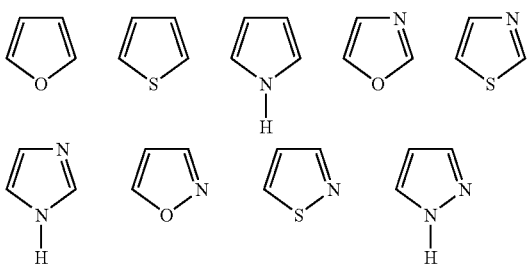

Furan Thiophene Pyrrole Oxazole Thiazole Imidazole Isoxazole Isothiazole Pyrazole

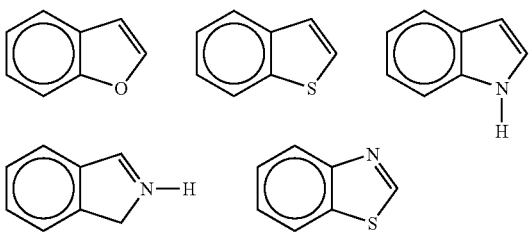

Benzo[b]furan Benzo[b]thiophene Indole 2H-Isoindole Benzothiazole

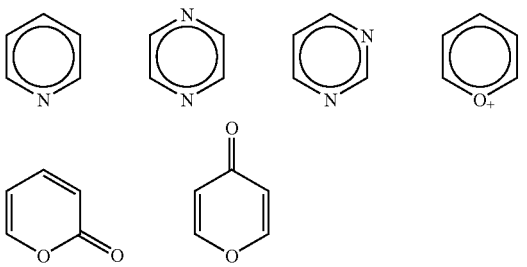

Pyridine Pyrazine Pyrimidine Pyrylium α-Pyrone γ-Pyrone

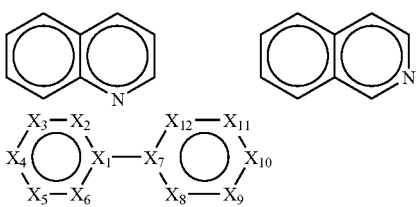

Quinoline Isoquinoline Bipyridine & derivatives (0-2 $X_i$/ring=N)

Preferably, the compound has one anchor group for binding to a substrate. The anchor group preferably has at least one silane, in particular a trichlorosilane, dichlorosilane, a monochlorosilane, a trialkoxysilane, a dialkoxysilane and/or a monoalkoxysilane.

A preferred embodiment of the molecule according to the invention has a substantially linear structure and the molecular group capable of a π-π interaction is arranged as a head group at that end of the compound which is remote from the anchor group. It is thus possible to produce monolayers having a particularly stable surface so that this can be structured by process steps.

The compound is preferably in the form of an ω-substituted alkylchlorosilane, alkoxysilanes, an ω-substituted alkanethiol and/or alkaneselenol, in particular phenoxyoctadecanethiol, and an analogous disulfide and selenide. In other embodiments, the compound is in the form of ω-phenoxyoctadecyltrichlorosilane, ω-biphenyloxyoctadecyltrichlorosilane and/or a thienyloctadecyltrichlorosilane.

In other embodiments, the compound has a dielectric group. Embodiments provide for the formation of a dielectric layer in a monolayer, which may be used in the production of semiconductor components (e.g. an OFET). Preferably, the dielectric group has at least one n-alkyl group with n=2 to 20. Alkyl groups advantageously have good dielectric properties.

In other embodiments of the invention, the monolayer is part of a layer structure. In still other embodiments of the invention, the layer structure may be part of a semiconductor component or may be a complete component.

Preferably, the monolayer is arranged on a substrate having a metallic surface, a metal oxide surface and/or a plastic surface. More preferably, the substrate has a surface containing hydroxyl groups, in particular a substrate comprising silicon, titanium or aluminum. Anchor groups bind in an efficient manner to these surfaces.

An embodiment of the invention provides a layer structure comprising a monolayer having anchor groups, which is bound to the substrate; above the anchor groups, viewed from the substrate, a layer of dielectric groups; and above the dielectric groups, a layer of molecular groups capable of a π-π interaction.

Preferably, the anchor group, the dielectric group and the molecular group capable of a π-π interaction are substantially the same length. Preferred embodiments advantageously provide for the formation of a uniform layer structure. In other embodiments, at least one further layer, preferably a metal layer, is arranged on a monolayer.

Embodiments of the invention provide semiconductor component having a layer structure. Preferably, the layer structure is formed according to embodiments of the invention. The semiconductor component may comprise an organic field effect transistor that has a monolayer having at least one dielectric layer.

Other embodiments of the invention provide a method for producing a layer structure, wherein the monolayer is deposited onto a substrate from a liquid phase or a gas phase. In the case of deposition from the gas phase (reduced pressure, elevated temperature), particularly high densities are obtained in the layers, which is advantageous.

In other embodiments the monolayer is deposited from a liquid phase with an organic solvent in an immersion process.

BRIEF DESCRIPTION OF THE DRAWINGS

The invention is explained in more detail below in several embodiments with reference to the figures of the drawings.

FIG. 12 shows a list of the experimental results (FIG. 5 to 9).

Table 1 shows a comparison of technology parameters between organic field effect transistors having a layer structure according to the invention and the data of the 170 nm node of Si technology.

The following list of reference symbols can be used in conjunction with the figures:

| | |
|---|---|
| 1 | Anchor group |
| 2 | Dielectric group |
| 3 | Group with a π—π interaction (head group) |
| 5 | Compound used to form a self-assembled layer |
| 10 | Substrate |
| 11 | Monolayer of molecules |
| 20 | Base substrate for OFET |
| 21 | Gate electrode |
| 22 | Gate dielectric layer |
| 23a | Source layer |
| 23b | Drain layer |
| 24 | Active semiconductor layer |
| 25 | Passivation layer |
| 100 | Semiconductor component (organic field effect transistor) |

DETAILED DESCRIPTION OF ILLUSTRATIVE EMBODIMENTS

Figure 1:
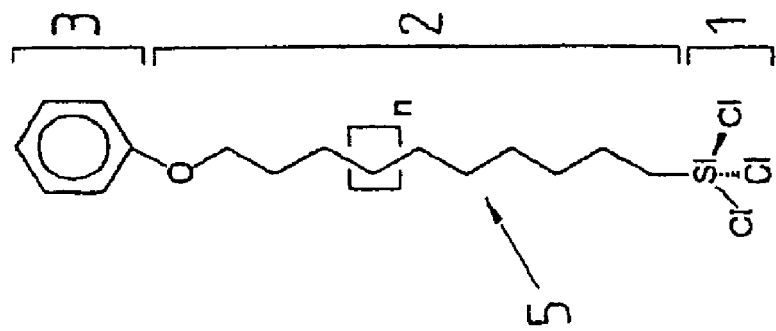
FIG. 1 shows a structural formula of an embodiment of the compound according to the invention.

FIG. 1 shows a structural formula for an embodiment of a compound 5 according to the invention. The compound 5 has a substantially linear structure. Arranged at one end is an anchor group 1 which in this case is in the form of trichlorosilane. This anchor group 1 permits binding to a substrate 10, which is not shown here (cf. FIG. 2). Arranged above the anchor group 1 is a dielectric group 2, which is in the form of n-alkyl. The chain length is n=2 to 20. A head group 3 having an aromatic system is arranged at that end of the compound 5, which is opposite the anchor group 1. This head group 3 permits a π-π interaction with other compounds of the same type and/or compounds of another type for stabilizing the monolayer (11).

Figure 2:
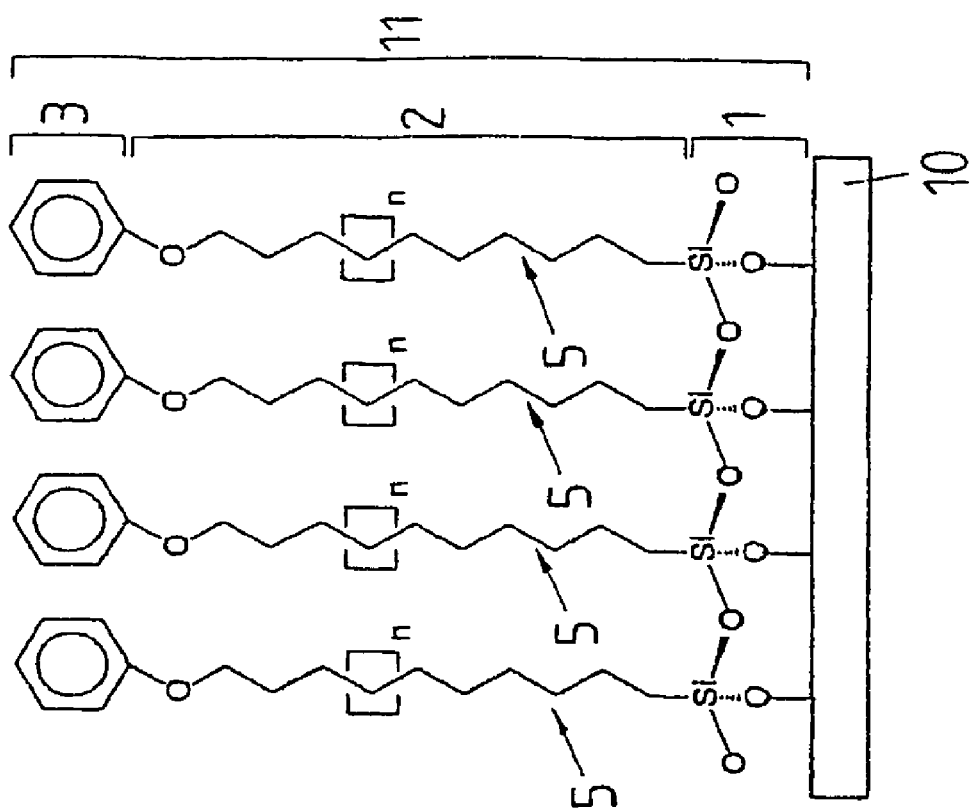
FIG. 2 shows a monolayer for the formation of a layer structure with an embodiment of the compound according to the invention on a substrate.

This is shown in FIG. 2, where compounds of the same type form a monolayer 11 which has a layer structure. Here, the anchor groups 1 of the molecules are bound to a hydroxyl-containing layer of a substrate 10. A π-π interaction can take place between head groups 3, so that an extremely stable layer structure forms.

Figure 3:
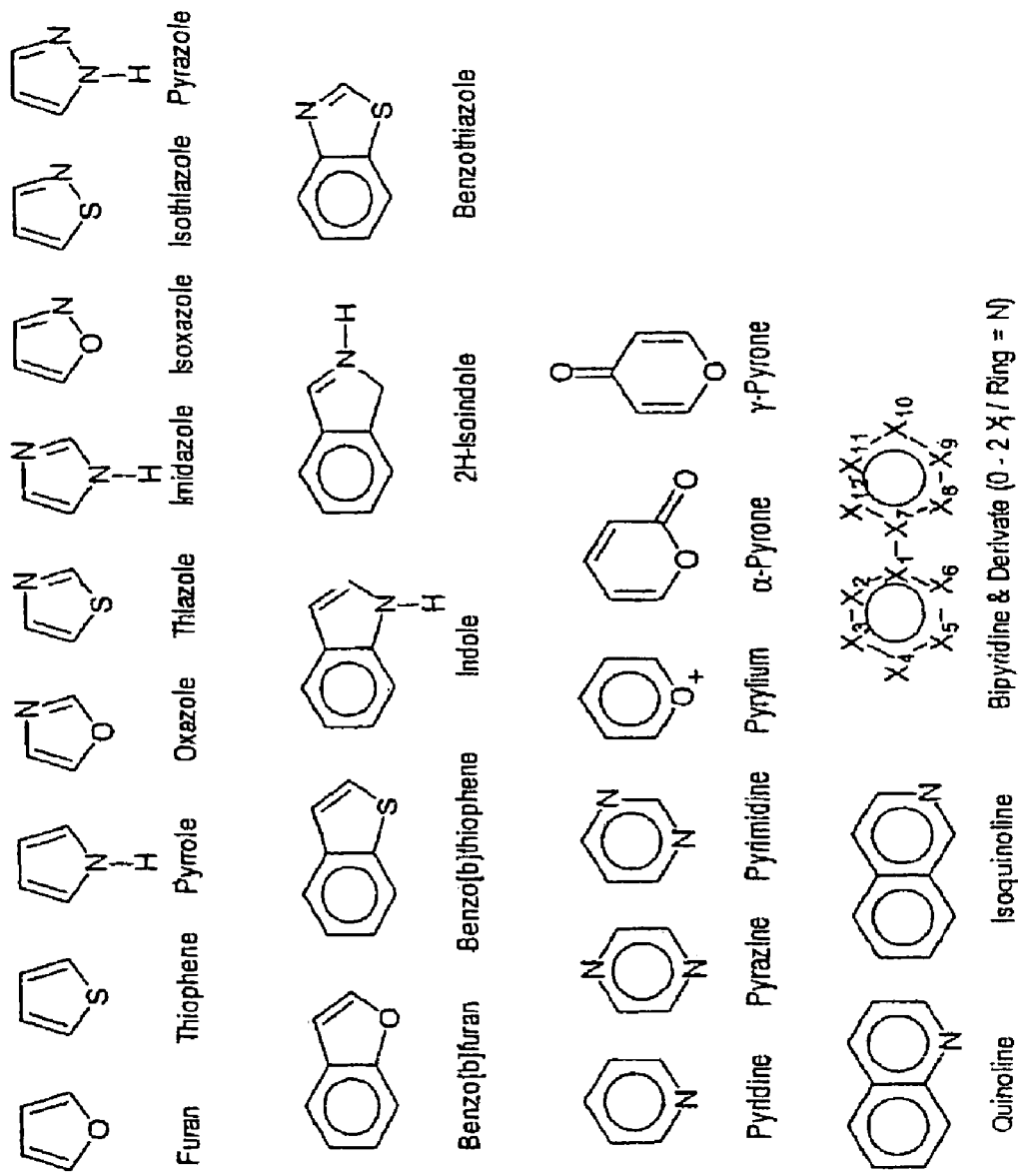
FIG. 3 shows head groups capable of a π-π interaction.

FIG. 3 shows alternative groups capable of a π-π interaction. It is also possible to use another aromatic compound, in particular a naphthalene, anthracene, naphthacene, pentacene, biphenyl, terphenyl, quaterphenyl and/or a quinquephenyl.

Chains having in each case different aromatic ring systems in the chain are also possible. The properties can be readily established via the length of the condensed chains. Smaller aromatics, which are generally not highly condensed and do not adversely affect the substantial monocrystalline or epitactic two-dimensional structure of the monolayer 11 are particularly suitable.

By means of these interactions, it is possible to form layers, which are suitable for dielectrics in organic field effect transistors. In direct comparison (cf. FIG. 5 to 9), it was possible to show that SAMs without this head group 3 have a very small process window or the material compatibility with subsequent layers is not guaranteed. Below, SAMs having head groups capable of π-π interactions are also referred to as T-SAMs.

The π-π interaction occurs spontaneously in the case of the monolayers 11 and need not be initiated. In principle, it is possible to introduce such groups for forming a π-π interaction even within the SAM, which groups, however, can then no longer be referred to as head groups.

The leakage currents of such T-SAMs are so low that they can be used as dielectrics for organic field effect transistors. Owing to their thickness of only about 3 nm, the supply voltage required for the operation of these transistors decreases to 1-2 V. If aromatic nature of the head groups is also responsible for the chemical inertness of the monolayers 11.

The advantages of these monolayers 11 (T-SAM) are explained in more detail below.

Chemical stability: The T-SAM is inert to all reagents, which do not destroy the bond to the substrate surface. The T-SAMs are resistant to aggressive reagents for a certain time since the reagents first have to diffuse through the monolayer 11 or have to attack it from the side. This robustness has not been observed to date in any other SAM class.

Process stability: The T-SAMs tolerate lithographic steps, such as the application of photoresist, photostructuring, wet development and the stripping of photoresist. It is thus possible to build up further layers for forming an organic field effect transistor, for example on dielectric layers.

Stability as a function of time and storage stability: There may be several weeks between the deposition and further processing without degradation of the T-SAM; the monolayers 11 are stable.

Metal deposition: Metals can be deposited electrochemically or via the gas phase onto the T-SAMs extensively in virtually 100% yield. This high dielectric "quality" was not observed to date in any other SAM class. Thus, when deposited on a SAM, no metals can be deposited by vapor deposition by octadecyltrichlorosilane (OTS) without short-circuit, while ω-phenoxyoctadecyltrichlorosilane forms such thick T-SAM layers that metal can be deposited by vapor deposition and structured over large areas at room temperature.

Thermal stability: T-SAMs are stable to temperatures above 200° C.

Homogeneity of layer thickness: The layer thickness obtained is an intrinsic function of the molecular geometry and of the anchoring on the substrate. There are virtually no variations in layer thickness.

Supply voltage of the transistors: A dielectric thickness of about 3 nm reduces the supply voltage required for operation to 1-2 V. A direct comparison between the 170 nm ITRS node of silicon technology and polymer electronics with the same dielectric thickness is summarized in table 1. The technology data are sufficient for a circuit design.

Flexibility in the choice of substrate: The compounds 5 are particularly suitable for deposition on surfaces containing hydroxyl groups, as naturally formed, for example, by silicon or aluminum in air. However, plastic surfaces, which are activated, for example, by plasma steps or etching methods, are also suitable. Silanes form Si—O bonds to the surfaces of the substrate 10. Particularly suitable silanes are tri-, di- or monochlorosilanes and tri-, di- or monoalkoxysilanes.

Particularly preferred as compounds in addition to ω-phenoxyoctadecyltrichlorosilane are ω-biphenyloxyoctadecyl-trichlorosilane and thienyloctadecyltrichlorosilane.

Figure 4:
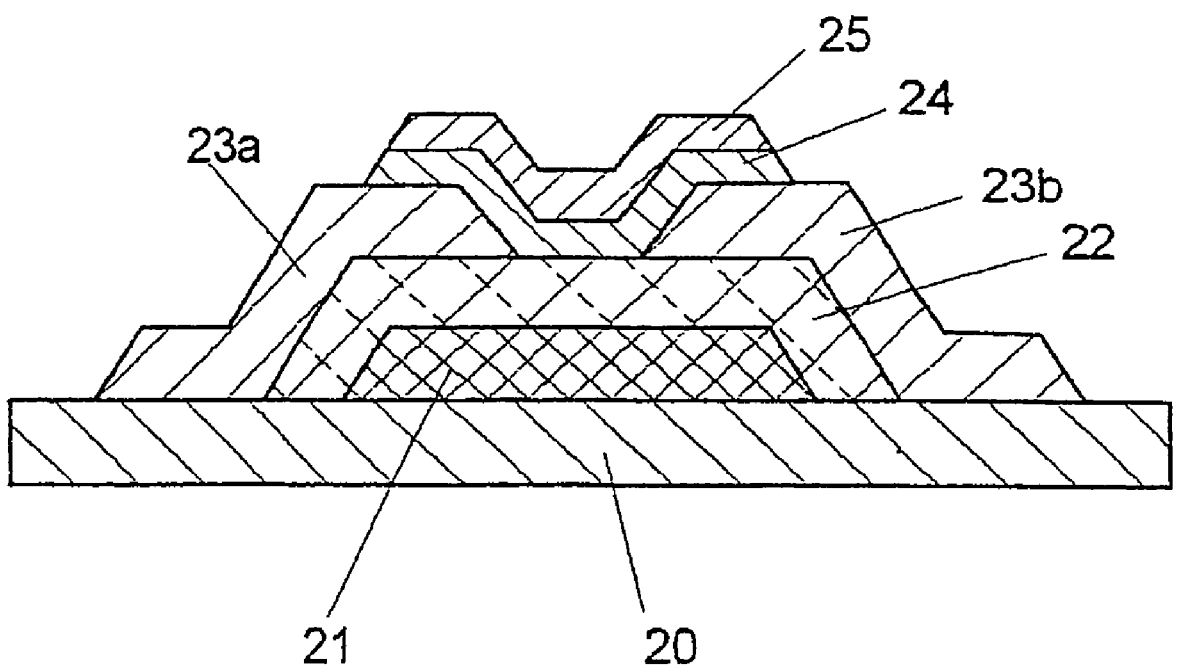
FIG. 4 shows the schematic structure of an organic field effect transistor.

In general, compounds capable of forming T-SAMs can also be bound to gold or copper by means of the SH coupling, to palladium by means of NC coupling or to hydrogen-terminated silicon by means of an aldehyde group. Before discussing embodiments of the layer structures according to the invention comprising monolayers 11, it is intended to explain the structure of an organic field effect transistor with reference to FIG. 4.

Organic field effect transistors are electronic components, which consist of a plurality of layers, all of which are structured, in order to generate integrated circuits by connections of individual layers. FIG. 5 shows the fundamental structure of such transistors in the bottom contact architecture.

Arranged on a base substrate 20 is a gate electrode 21, which is covered by a gate dielectric layer 22. Such a gate dielectric layer 22 may consist, for example, of a monolayer 11 described above. Such dielectrics have a layer thickness of less than 5 nm (bottom up).

Arranged on the gate dielectric layer 22 are a source layer 23a and a drain layer 20b, both of which are connected to an active semiconducting layer 24 on top. A passivation layer 25 is arranged above the active layer 24.

Examples which describe the function of embodiments of the invention are described below.

For this purpose, organic field effect transistors in the so-called top contact (FIGS. 5A and 5B) or bottom contact architecture (FIG. 5c) were produced for evaluating the monolayers 11 according to the invention (T-SAMs).

In the case of the top contact architecture, the source and drain electrodes (23a, 23b) are present above the organic semiconductor 25 and in the case of the bottom contact architecture said electrodes are present in the same plane as the organic semiconductor 25.

For this purpose, known monolayers (SAM) and monolayers according to the invention (T-SAM) were deposited on a gate electrode material 21 as a substrate.

Figure 5A:
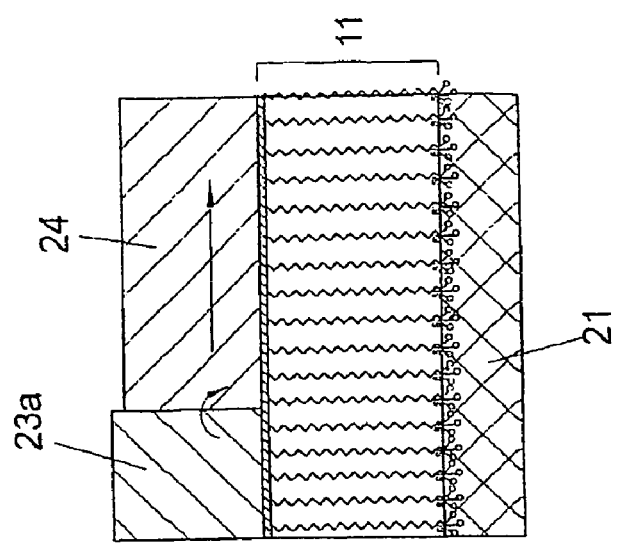
FIG. 5A-C show three variants of a layer structure for an organic field effect transistor.
Figure 5B:
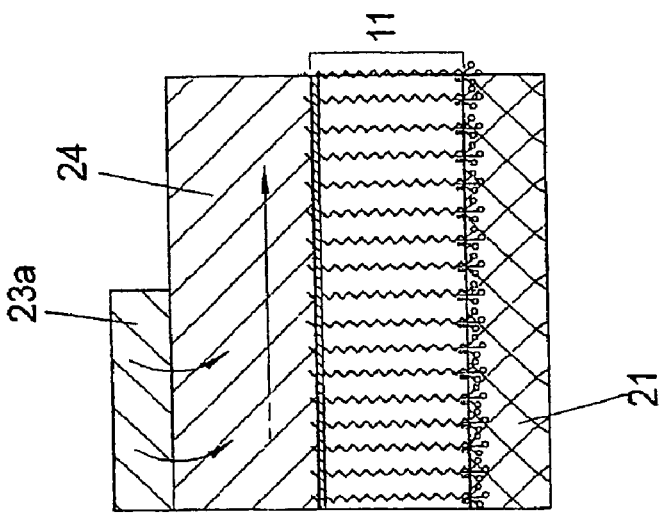
Figure 5C:
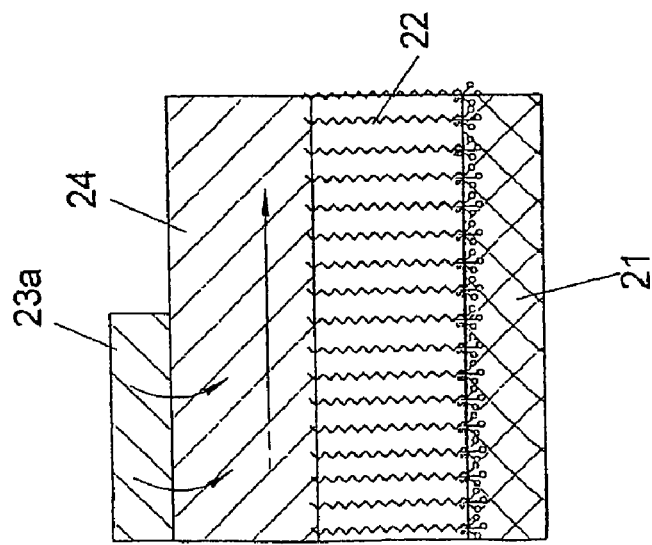

These experimental variants are shown schematically in FIG. 5a to 5c. For the sake of simplicity, the drain contact is omitted in FIG. 5a to 5c.

FIG. 5a shows a known monolayer (SAM) comprising dielectric material 22, which is used in a top contact architecture. The monolayer (SAM), the semiconducting layer 24 and the source contact 23a were applied by thermal vapor deposition.

FIG. 5b shows the same structure as FIG. 5a, except that here an embodiment of the layer structure according to the invention comprising a monolayer 11 is arranged on the gate electrode material 21.

FIG. 5c shows an embodiment in which an embodiment of the layer structure according to the invention comprising a monolayer 11 is used. Here, however, the source contact 23a is formed in a bottom contact architecture.

The results of measurements will be discussed below, the numerical values of the experiments being summarized in FIG. 12.

EXAMPLE 1

SAM

An SAM comprising octadecyltrichlorosilane (OTS) was deposited from the gas phase onto a highly doped wafer as gate electrode material 21. Thereafter, in each case 30 nm organic semiconductor layers 24 comprising a. pentacene or b. α,ω-bisdecylsexithienyl were deposited from the gas phase. 30 nm of gold were deposited on the layer 24 of the organic semiconductor via a shadow mask as source and drain electrode (23a, 23b).

Figure 6C:
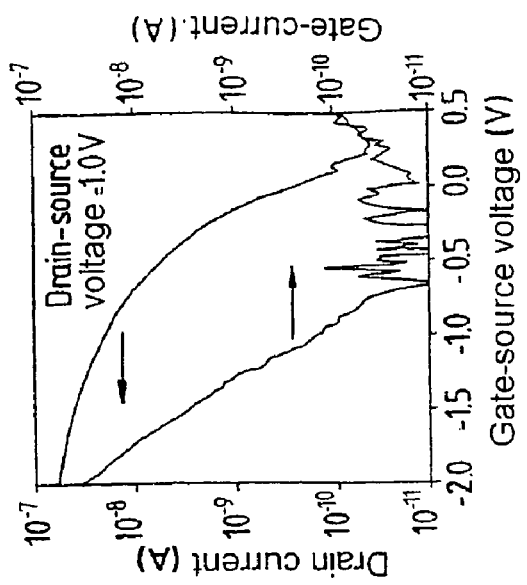
FIG. 6A-C show characteristics of a transistor without a layer structure according to the invention, having a silicon gate electrode.
Figure 6B:
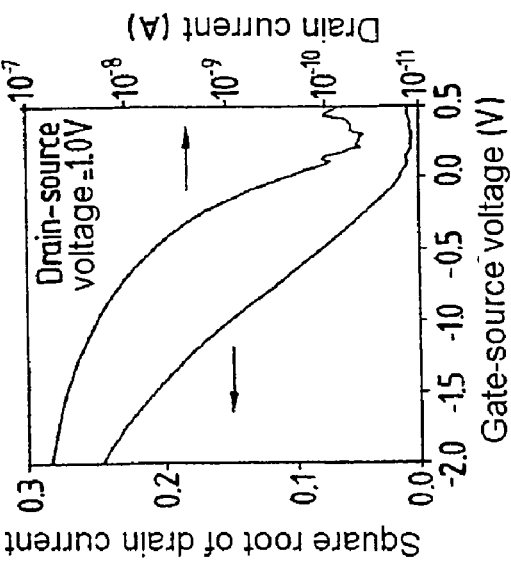
Figure 6A:
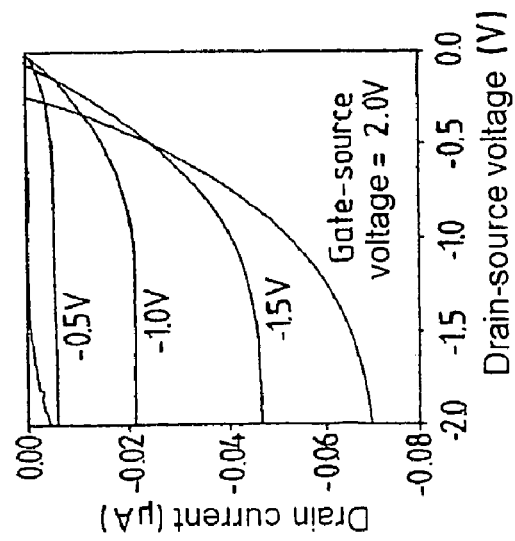

Result:

a. In the case of pentacene, no organic field effect transistors were obtained (FIG. 2, experiment UZ-36).

b. In the case of α,ω-bisdecylsexithienyl (FIG. 2, experiment ZU-35), it was possible to obtain field effect transistors. This is due to the special alkyl-alkyl interaction of the sexithiophene and the SAM. The characteristics obtained are shown in FIG. 6a to 6c.

Transistor characteristics:

$L = 130$ μm $W = 170$ μm $t_{SAM} = 2.5$ nm $E_{SAM} = 2.5$ $\lambda = 0.04$ cm$^2$/Vs (carrier mobility)

Threshold voltage=0 V

Subthreshold slope=200 mV/decade on/off current ratio=$10^3$ drain/gate current ratio=1.6.

In the case of the SAM, the presence of field effect transistor behavior evidently depends on the organic semiconductor material chosen.

Figure 7B:
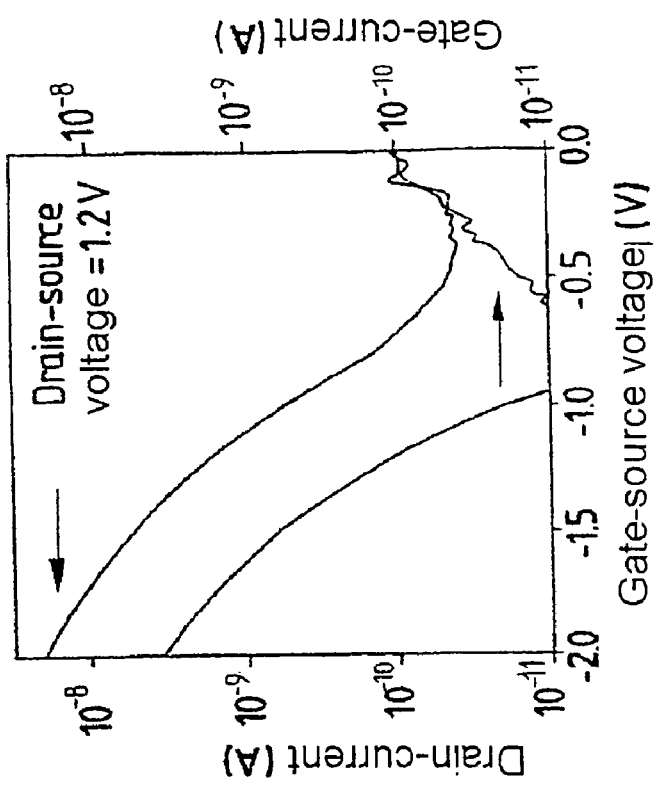
FIGS. 7A, B show characteristics of a transistor without a layer structure according to the invention, having an aluminum gate electrode.
Figure 7A:
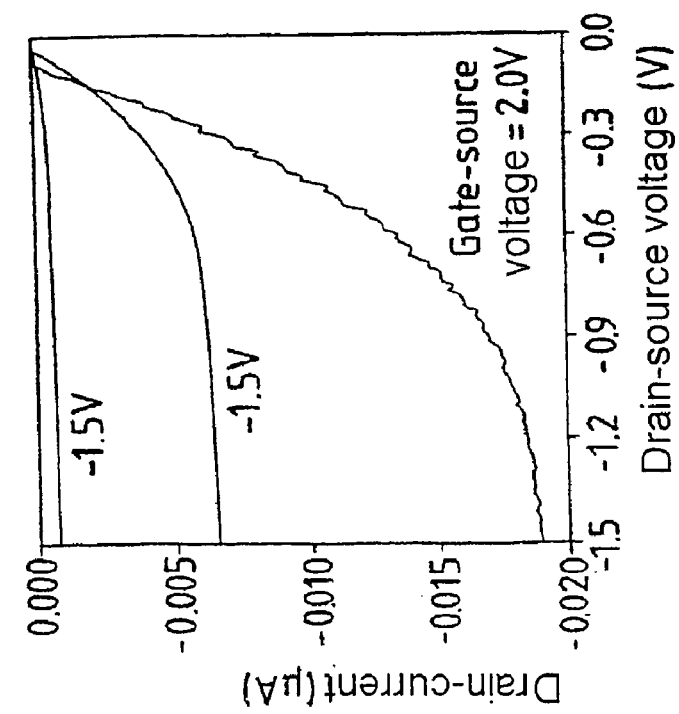

Control experiments show that the transistor functionality is obtained only in the case of a deposited SAM. A natural oxide layer on silicon is not sufficient in this case (FIG. 2, experiment UZ-37). As an alternative to silicon as substrate 11, the OTS SAM also forms on aluminum. The characteristics are shown in FIGS. 7a and 7b (FIG. 2, experiment ZU-43). The layer thickness of the OTS SAM is 2.5 nm. The other parameters are:

$L = 130$ μm $W = 170$ μm $\mu = 0.03$ cm$^2$/Vs (carrier mobility)

Threshold voltage=−0.9 V

Subthreshold slope=360 mV/decade on/off current ratio=$10^3$

For complete integration, the electrodes cannot be defined by shadow masks, owing to the limitation of the resolution. The bottom contact transistor architecture is suitable for fine structuring. However, bottom contact transistors having an OTS SAM as gate dielectric showed only short-circuits between source/gate and drain/gate.

EXAMPLE 2

T-SAM

In example 2, the behavior or an embodiment of the layer structure according to the invention is investigated.

In contrast to example 1, here ω-phenoxyoctadecyl-trichlorosilane permits the production of organic field effect transistors in top and bottom contact architecture, independently of the organic semiconductor. This behavior demonstrates the extreme stability and quality of the T-SAMs.

For the preparation of the top contact architecture (cf. FIG. 5b), a T-SAM was applied from liquid phase to a highly doped silicon substrate 21. Alternatively, application from the gas phase analogous to example 1 is also possible. The top contact transistor were then produced in the same manner as described in example 1:

Vapor deposition of the organic semiconductor pentacene; definition of the metal contacts comprising gold—by shadow mask/vaporization.

Figure 8C:
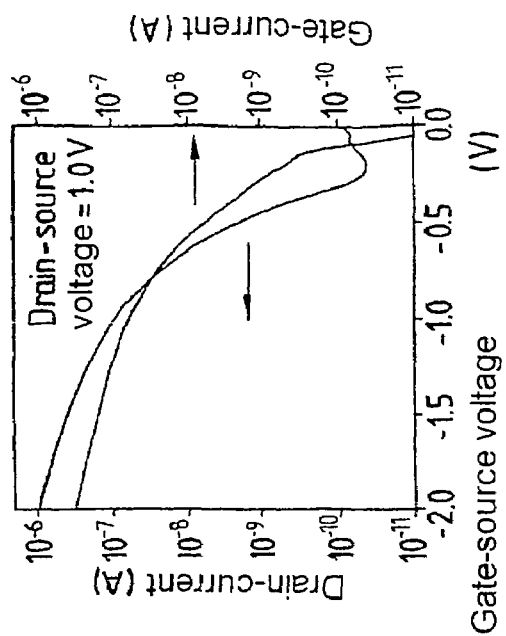
FIG. 8A-C show characteristics of a transistor comprising a first embodiment of a layer structure according to the invention (top contact architecture)
Figure 8B:
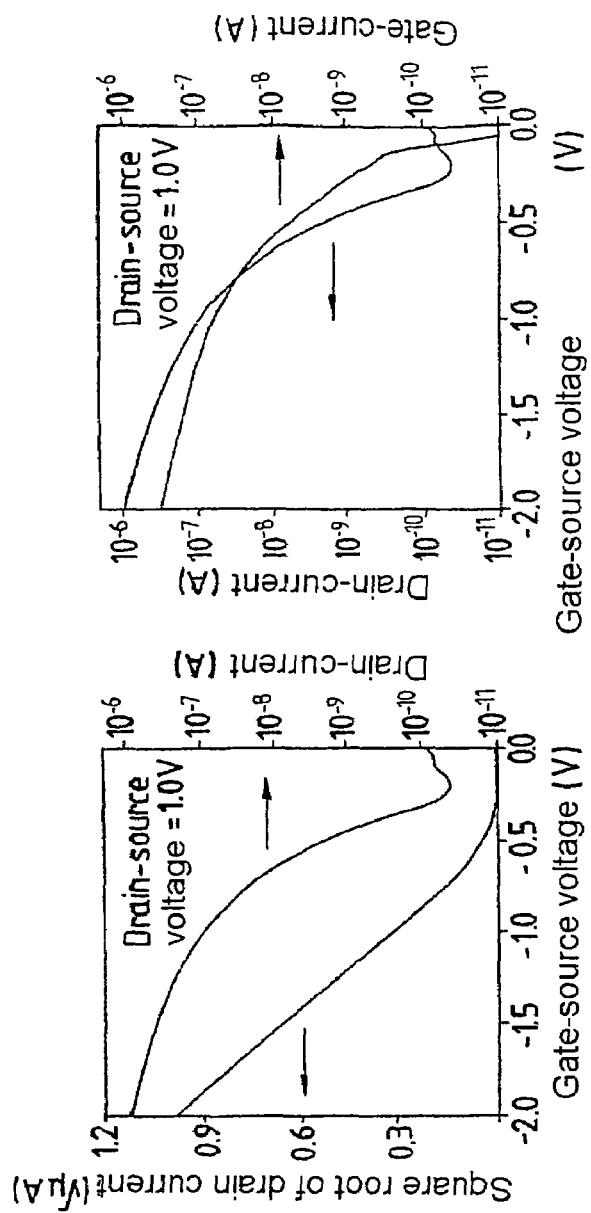
Figure 8A:
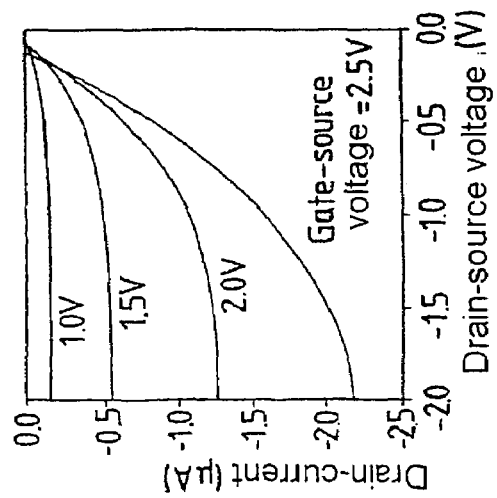

The characteristics of an organic field effect transistor produced in this manner are shown in FIG. 8a to 8c (FIG. 2, experiment UZ-31). The characteristics are:

L=130 μm

W=170 μm $t_{SAM}$=2.5 nm $E_{SAM}$=2.5

μ=0.9 $cm^2$/Vs (carrier mobility)

Threshold voltage=−0.6 V

Subthreshold slope=135 mV/decade on/off current ratio=$10^4$

The high quality of the T-SAM layer of the layer structure according to the invention compared with the OTS SAM is evident here since, in the case of a top contact structure with OTS SAM and pentacene as semiconductor, no field effect could be observed (cf. example 1 point a).

Metals can be deposited from the gas phase on T-SAMs at room temperature and can be photolithographically structured.

Figure 9C:
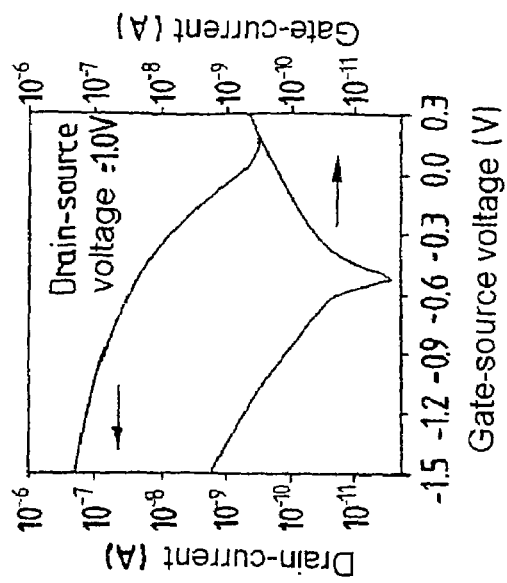
FIG. 9A-C show characteristics of a transistor comprising a second embodiment of a layer structure according to the invention (bottom contact architecture)
Figure 9B:
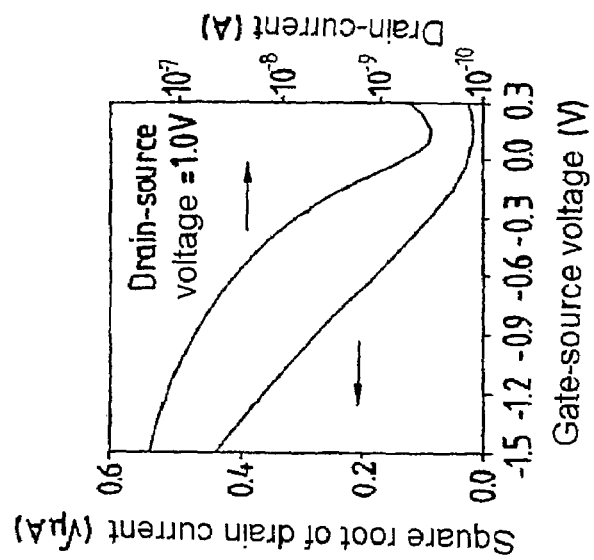
Figure 9A:
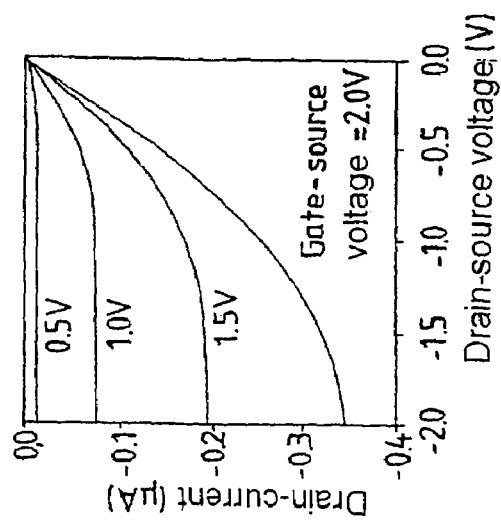

Organic field effect transistors in bottom contact architecture which can be integrated to form circuits can thus be obtained, the characteristics of the transistors are shown in FIG. 9a to 9c (FIG. 2, experiment UZ-33). Channel length and width can be adapted to the respective requirements.

For this purpose, a T-SAM is applied from the liquid phase to a highly doped silicon substrate 21 (alternatively, application from the gas phase analogously to example 1 is also possible). A 30 nm thick gold layer is subsequently deposited thereon by vapor deposition. The source and drain contacts 23a, 23b are defined on said gold layer photolithographically and etched by a wet chemical method ($I_2$/KI solution). The contacts are cleaned by means of acetone in order to remove the photoresist etch mask. The organic semiconductor (pentacene) is then deposited.

Transistor characteristics UZ-33 (cf. FIG. 2):

L=5 μm

W=5 μm $t_{SAM}$=2.5 nm $E_{SAM}$=2.5

μ=0.2 $cm^2$/Vs (carrier mobility)

Threshold voltage=−0.1 V

Subthreshold slope=240 mV/decade on/off current ratio=$10^3$ drain/gate current ratio=100.

EXAMPLE 3

T-SAM with Semiconductor from Liquid Phase

As an alternative to the vapor deposition of the organic semiconductors, organic semiconductors can also be applied from the liquid phase.

For this purpose, the procedure in UZ-33 (example 2, bottom contact) is adopted. Instead of pentacene, a 1% solution of poly-3-hexylthiophene in chloroform is applied by spin coating for 10 seconds at 2000 revolutions and dried at 60° C. for 10 min on a hotplate.

EXAMPLE 4

If, instead of the ω-substituted alkyltrichlorosilanes, other suitable compounds, in particular ω-substituted alkanethiols and alkaneselenols, such as 18-phenoxyoctadecanethiol, and the analogous disulfides and diselenides are used, insulating SAMs can be produced on metals. Platinum, palladium, copper, silver, gold and mercury are suitable for this purpose.

The metal substrate is coated by immersion in an ethanolic solution of the SAM-forming compound. The layers thus obtained can be contacted by vapor deposition of metals or by electrolyte and exhibit good insulation properties. The current density measured at 1.5 V (gold, 18-phenoxyoctadecanethiol) was 7.4 A/$m^2$.

Further experiments showed that the deposition from the gas phase (reduced pressure, elevated temperature) gives better layers than deposition from solution. In FIG. 12, this is evident from the values for $I_D/I_G$ and $I_G$ of the experiments MH-357, MH 362 (gas phase) in comparison with UZ-31, UZ-33 (liquid phase).

Figure 10B:
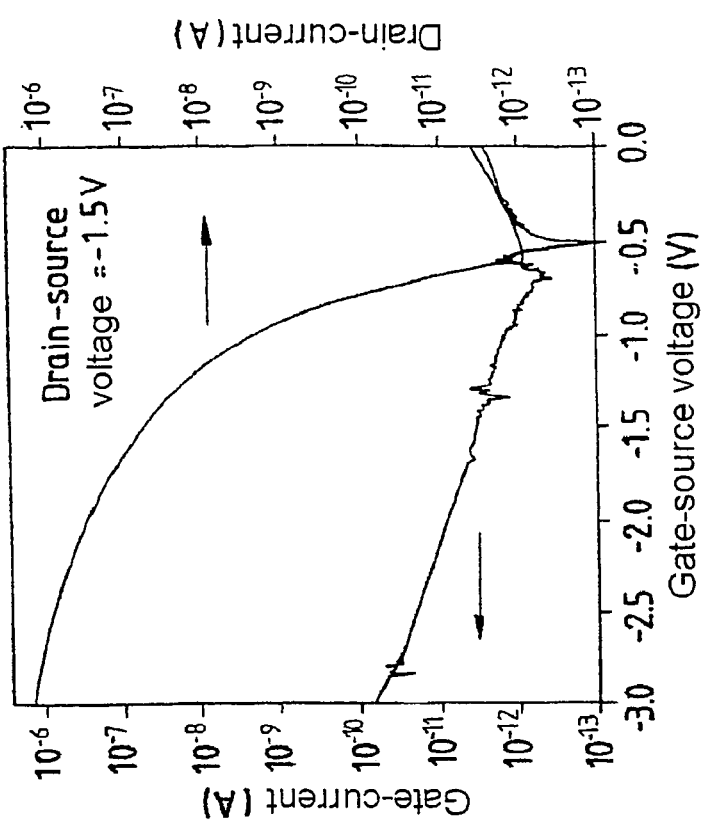
FIGS. 10A, B show characteristics of a transistor comprising a third embodiment of a layer structure according to the invention (deposition from the gas phase)
Figure 10A:
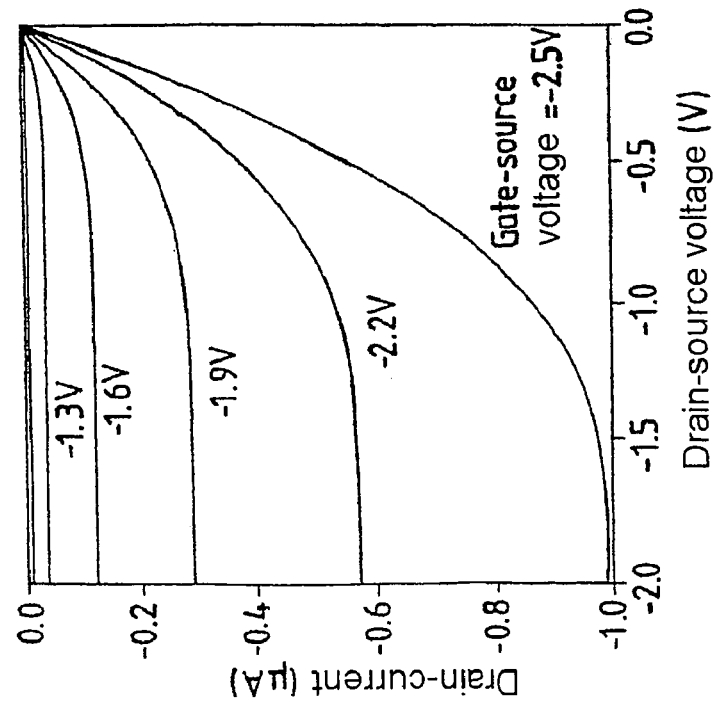
Figure 11B:
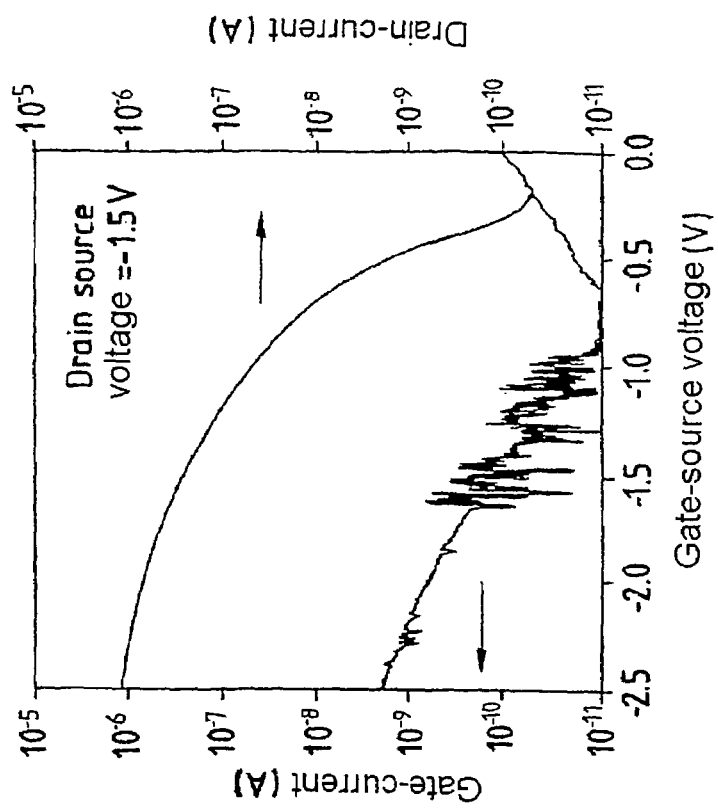
FIGS. 11A, B show characteristics of a transistor comprising a fourth embodiment of a layer structure according to the invention (deposition from the gas phase)
Figure 11A:
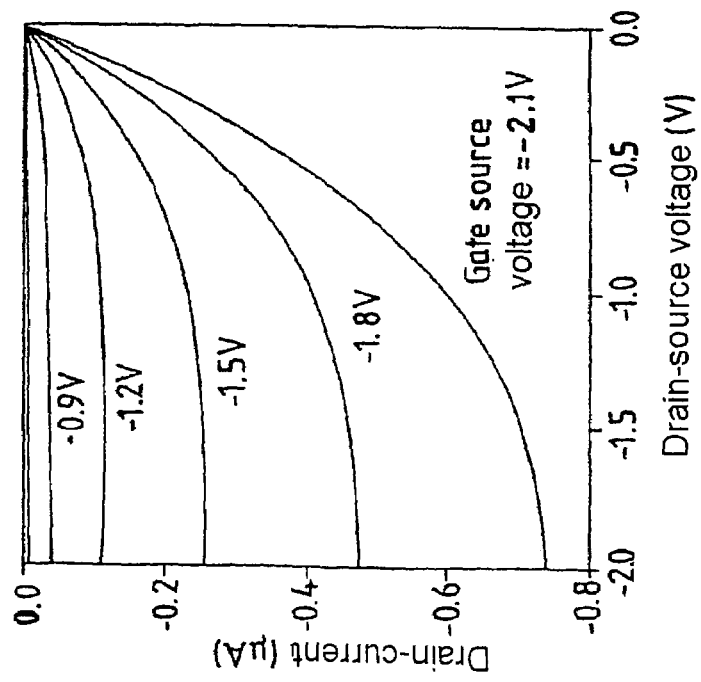

The characteristics of the transistor for the embodiment according to experiment MH-357 (top contact) are shown in FIGS. 10a, 10b; the characteristics of the transistor for the embodiment according to experiment MH-362 (bottom contact) are shown in FIGS. 11a, 11b.

The invention is not limited in its execution to the above-mentioned preferred embodiments. However, a number of variants is conceivable which makes use of the compound according to the invention, the layer structure according to the invention, the semiconductor component according to the invention and the method according to the invention, also in versions of fundamentally different types.

TABLE 1

| TECHNOLOGY PARAMETER | T-SAM transistor | 170 nm ITRS node TFTs |
|---|---|---|
| Dielectric thickness | 2.5 | 2.5 |
| Channel length, μm | 5 | 0.12 |
| Carrier mobility, cm$^2$/V-s | >1 | <500 |
| Operating voltage, V | 1.5 | 1.8 |
| Threshold voltage, V | −0.1 | ~0.3 |
| Subthreshold swing, mV/dec | 135 | 70 |
| Gate fault current, nA/μm | <0.05 | 7 |
| On-state drain current, μA/μm | >0.02 | 750 |
| On/off current ratio | >10$^4$ | 10$^5$ |

What is claimed is:

1. A semiconductor component comprising:
   a gate electrode layer adjacent a substrate;
   a gate dielectric layer adjacent the gate electrode layer, wherein the gate dielectric layer comprises a monolayer of at least one compound, wherein the compound has an aromatic or a condensed aromatic molecular group, the molecular group being capable of a π-π interactions;
   a source layer adjacent the gate electrode layer;
   a drain layer adjacent the gate electrode layer;
   an organic semiconductor layer adjacent the gate electrode layer; and
   a passivation layer adjacent the organic semiconductor layer.

2. The semiconductor component of claim 1, wherein the semiconductor component is an organic field effect transistor (OFET), and the monolayer comprises at least one dielectric layer.

3. The semiconductor component of claim 1, wherein the molecular group capable of π-π interactions is selected from the group consisting essentially of a naphthalene, anthracene, naphthacene, pentacene, biphenyl, terphenyl, quaterphenyl, quinquephenyl, and combinations thereof.

4. The semiconductor component of claim 1, wherein the molecular group capable of π-π interactions is selected from the group consisting essentially of:

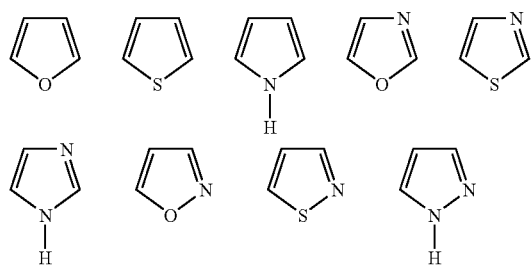

Furan Thiophene Pyrrole Oxazole Thiazole Imidazole Isoxazole Isothiazol Pyrazole

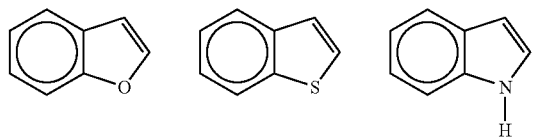

Benzo[b]furan Benzo[b]thiophene Indole 2H-Isoindole Benzothiazole

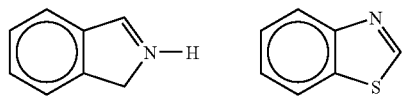

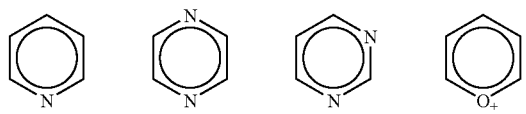

Pyridine Pyrazine Pyrimidine Pyrylium α-Pyrone γ-Pyrone

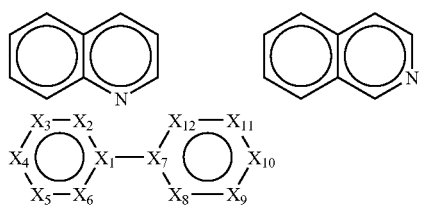

Quinoline Isoquinoline Bipyridine & derivatives (0-2 X$_i$/ring=N), and combinations thereof.

5. The semiconductor component of claim 1, wherein the compound has at least one anchor group, wherein the anchor group binds to the substrate.

6. The semiconductor component of claim 5, wherein the the anchor group has at least one silane.

7. The semiconductor component of claim 6, wherein the silane is selected from the group consisting essentially of a trichlorosilane, dichlorosilane, a monochlorosilane, a trialkoxysilane, a dialkoxysilane, a monoalkoxysilane, and combinations thereof.

8. The semiconductor component of claim 6, wherein compound has a substantially linear structure and the molecular group capable of a π-π interactions is arranged at an end of the linear structure remote from the anchor group.

9. The semiconductor component of claim 1, wherein the compound is selected from the group consisting essentially of a -substituted alkyltrichlorosilane, a -substituted alkanethiol, a alkaneselenol, disulfides and selenides thereof, and combinations thereof.

10. The semiconductor component of claim 1, wherein the compound is selected from the group consisting essentially of an -phenoxyoctadecyltrichlorosilane, -biphenyloxyoctadecyltrichlorosilane, a phenoxyoctadecanethiol, a thienyloctadeclytrichlorosilane, and combinations thereof.

11. The semiconductor component of claim 1, wherein the compound has a dielectric group for forming the dielectric layer.

12. The semiconductor component of claim 11, wherein the dielectric group has at least one n-alkyl group with n=2 to 20.

13. The semiconductor component of claim 1, wherein the monolayer is arranged on the substrate, the substrate having a surface, wherein the surface is selected from the group consisting essentially of a metallic surface, a metal oxide surface, a plastic surface, and combinations thereof.

14. The semiconductor component of claim 13, wherein the surface has hydroxyl groups.

15. The semiconductor component of claim 14, wherein the substrate is silicon or aluminum.

16. The semiconductor component of claim 1, further comprising:
anchor groups bonding the monolayer to the substrate;
a layer of dielectric groups arranged above the anchor groups; and
a layer of molecular groups capable of a $\pi$-$\pi$ interaction arranged above the dielectric groups.

17. The semiconductor component of claim 16, wherein the anchor group, the dielectric group, and the molecular group capable of the $\pi$-$\pi$ interaction are substantially the same length.

18. The semiconductor component of claim 16, wherein a metal layer is arranged on the monolayer.

19. A semiconductor component of claim 1, wherein the monolayer is deposited on the substrate from a liquid phase or a gas phase.

20. The semiconductor component of claim 19, wherein the monolayer is deposited from a liquid phase with an organic solvent in an immersion process.

* * * * *

UNITED STATES PATENT AND TRADEMARK OFFICE
CERTIFICATE OF CORRECTION

PATENT NO. : 7,298,013 B2 Page 1 of 1
APPLICATION NO. : 11/313250
DATED : November 20, 2007
INVENTOR(S) : Schmid et al.

It is certified that error appears in the above-identified patent and that said Letters Patent is hereby corrected as shown below:

On the title page item (75), delete "Schutz," and insert --Schuetz,--.

Signed and Sealed this

Fifteenth Day of April, 2008

JON W. DUDAS
*Director of the United States Patent and Trademark Office*